United States Patent [19]
Goettsche et al.

[11] Patent Number: 6,110,263
[45] Date of Patent: Aug. 29, 2000

[54] TIMBER PRESERVING AGENT FOR MAINTENANCE PURPOSES

[75] Inventors: Reimer Goettsche, Baden-Baden; Wendelin Hettler, Sinzheim; Michael Breuer, Rottenburg; Hans-Peter Seelmann-Eggebert, Limburgerhof, all of Germany

[73] Assignee: Dr. Wolman GmbH, Sinzheim, Germany

[21] Appl. No.: 09/125,978

[22] PCT Filed: Feb. 28, 1997

[86] PCT No.: PCT/EP97/00966

§ 371 Date: Aug. 28, 1998

§ 102(e) Date: Aug. 28, 1998

[87] PCT Pub. No.: WO97/32700

PCT Pub. Date: Sep. 12, 1997

[30] Foreign Application Priority Data

Mar. 5, 1996 [DE] Germany .......................... 196 08 435

[51] Int. Cl.[7] .............................. B27K 3/52; B27K 5/00; A01N 59/20
[52] U.S. Cl. ................ 106/18.32; 106/18.3; 106/18.31; 424/404; 424/405; 424/414; 424/443; 424/447; 424/630; 424/632; 424/633; 424/634; 424/635; 424/637; 424/638; 427/4; 427/393; 427/397

[58] Field of Search ................................ 106/18.3, 18.31, 106/18.32; 424/404, 405, 414, 443, 447, 630, 632, 633, 634, 635, 637, 638; 427/4, 393, 397

[56] References Cited

U.S. PATENT DOCUMENTS

| | | | |
|---|---|---|---|
| 4,761,179 | 8/1988 | Goettsche et al. | 106/18.32 |
| 4,857,322 | 8/1989 | Goettsche et al. | 424/633 |
| 5,276,029 | 1/1994 | Goettsche et al. | 106/18.3 |
| 5,342,438 | 8/1994 | West | 106/18.3 |

FOREIGN PATENT DOCUMENTS

| | | |
|---|---|---|
| 3743821 | 7/1989 | Germany . |
| 96/23635 | 8/1996 | WIPO . |
| 96/23636 | 8/1996 | WIPO . |

OTHER PUBLICATIONS

Richardson, *Wood Preservation*, The Construction Press Ltd., p. 181. (1978) (no month).

*Primary Examiner*—Anthony Green
*Attorney, Agent, or Firm*—Keil & Weinkauf

[57] ABSTRACT

The use of a wood preservative for the afterprotection of wood, comprising a copper compound, a polyamine and an inorganic fungicide, and a bandage for the afterprotection of wood, which contains this wood preservative, is described.

23 Claims, No Drawings

TIMBER PRESERVING AGENT FOR MAINTENANCE PURPOSES

The present invention relates to the use of a wood preservative for the afterprotection of wood, comprising a copper compound, a polyamine and an inorganic fungicide, and a bandage for the afterprotection of wood, which contains this wood preservative.

For the aftercare of transmission-line poles in the supply network of the post office and electricity supply companies or similar round wood stocks, in particular in the area of the ground-air zone, bandages containing water-soluble wood preservatives are applied. It is known to employ water-soluble salts based on inorganic fluorine compounds for this, such as, for example, alkali metal fluorides, in some cases in combination with alkali metal bichromate or boron compounds such as boric acid or borax. These salts, however, are exclusively active against wood-destroying Basidiomycetes, the soft rot activity for installation with soil contact is absent. Proposed substances having soft rot activity are, on the one hand, dinitrophenol (Barry A. Richardson: Wood preservation—The Construction Press Ltd., Lancaster p. 181) or combinations of the abovementioned compounds with water-soluble copper salts such as, for example, copper sulfate or copper acetate. Mixtures of copper sulfate, also in combination with alkali bichromate, with boric acid and copper acetate with alkali metal fluoroborates are prior art. Dinitrophenol has meanwhile been excluded because of its toxicity.

The water-soluble abovementioned copper compounds on their own, but also in the abovementioned combinations, do not have good diffusion power adequate to penetrate, for example, the sapwood of pine poles, even on long standing, and to reach the core.

Wood preservatives based on copper and amines as complexing agents have been proposed for large-scale impregnation, in particular boiler pressure impregnation.

EP-B 211 181 relates to a wood preservative based on a copper salt and monoethanolamine for the boiler pressure impregnation of wood.

EP-B 270 848 describes a wood preservative based on a copper compound, a carboxylic acid and an aliphatic polyamine for boiler pressure impregnation.

EP-A 423 674 describes a wood preservative based on a metal salt of an N-organyldiazeniumdioxy compound and a complex-forming polymeric amine for the boiler pressure process.

It is common to all the wood preservatives described above that they have a high fixing power for the copper in the wood. By means of this, the diffusion power of the copper is restricted, which is why these systems are unsuitable for the afterprotection of wood.

Known, currently used systems for the afterprotection of wood contain, for example, combinations of copper naphthenate, boron and fluorine compounds. An example of this type of product, which is mainly used in the USA, is CURAP 20 (manufacturer: naK Biotech), a paste which contains 18.16% of amine-based copper naphthenate and 40% of sodium tetraborate decahydrate. Investigations on poles (species of wood Douglas fir or pine) which had been treated with this product showed after a service life of from 1 to 3 years that copper for the major part is virtually only distributed near to the surface (0–10 mm) in the wood (with investigated penetration depths of up to 25 mm) and these products thus only have a very restricted diffusion power for copper (Conserving energy by environmentally acceptable practices in maintaining and procuring transmission poles. 15th annual report, September 1995, J. J. Morrell, Oregon State University, Corvallis, Oreg.).

The subsequently published WO 96/233636 describes wood preservatives in paste form, which comprise a fungicidal metal compound and a fungicidal boron compound. The metal compounds also include copper complexed with aminocarboxylic acids or polycarboxylic acids.

The subsequently published WO 96/233635 describes a wood preservative which comprises a metal chelate. Copper complexes with amino acids, iminodiacetic acid, ethylenediaminotetraacetic acid, dicarboxylic acids and polyphosphates are described.

It is an object of the present invention to make available a wood preservative for the afterprotection of wood, which has a good diffusion power of the copper in the wood, with good protection at the same time against soft rot and Basidiomycetes.

It is a further object of the present invention to make available a bandage which contains this wood preservative for the afterprotection of wood.

We have found that this object is achieved by a wood preservative based on a copper compound, a polyamine and an inorganic fungicide, if appropriate a complex-forming organic carboxylic acid or its ammonium or alkali metal salts, if appropriate further auxiliaries and if appropriate water for the afterprotection of wood.

These wood preservatives are particularly suitable for the afterprotection and the aftercare of wood and are used as bandages, in the inoculation injection process, borehole process and paste process. They penetrate the sapwood in the presence of moisture, e.g. soil contact, and have a good deep action.

Copper compounds which can be used are water-soluble or -insoluble compounds, e.g. copper sulfate, copper acetate, copper citrate, copper naphthenate, copper hydroxide, copper hydroxycarbonate, copper oxychloride, copper oxide, copper borate, copper fluoride, copper fluoroborate, bis(N-cyclohexyldiazeniumdioxy) copper or mixtures thereof.

Copper hydroxycarbonate, copper hydroxide and mixtures thereof are preferred.

Copper hydroxide, especially stabilized copper hydroxide (Norddeutsche Affinerie), is particularly preferably used.

The action of the wood preservative can be improved by salts of N-cyclohexyldiazenium dioxide and other diazenium dioxides, e.g. as the potassium salt, with copper compounds the abovementioned bis(N-cyclohexyldiazeniumndioxy)copper generally being formed.

The mixtures contain from 0.25 to 20% by weight of copper calculated as the element. Some of the copper can also be replaced, for example, by a corresponding zinc compound.

Polyamines which can be used are alkyleneamines having 3–9 C atoms and 2–4 N atoms such as, for example, ethylenediamine, 2-diethylaminoethylamine, diethylenetriamine, triethylenetetramine, tetraethylenepentamine, 1,2-diaminopropane, 1,3-diaminopropane, dipropylenetriamine, tripropylenetetramine, 3-(2-aminoethyl)aminopropylamine, N,N'-bis(3-aminopropyl-1,3-propanediamine and alkanolamines such as, for example, aminoethylethanolamine, and mixtures thereof.

Ethylenediamine, diethylenetriamine, 1,3-diaminopropane, dipropylenetriamine, aminoethylethanolamine and mixtures thereof are preferred.

Suitable inorganic fungicides are boron compounds such as alkali metal borates, aminoborates, boric acid, boric acid esters and $B_2O_3$; fluorides such as alkali metal fluorides, alkali metal bi-fluorides, silicon fluorides, ammonium fluorides, ammonium hydrogen fluorides; fluoroborates; fluorophosphates; difluorophosphiates and mixtures thereof.

Sodium fluoroborate, potassium fluoroborate, boric acid, sodium fluoride and mixtures thereof are preferred.

Furthermore, complex-forming organic carboxylic acids such as hydroxycarboxylic acids, aminocarboxylic acids, nitrogen-containing polycarboxylic acids, ammonium or alkali metal salts thereof and mixtures thereof can additionally be used.

Suitable hydroxycarboxylic acids which can additionally be used are, for example, glycolic acid, lactic acid, tartaric acid, citric acid, malic acid, ammonium or alkali metal salts thereof and mixtures thereof.

Amino acids such as, for example, glycine, sarcosine, ammonium or alkali metal salts thereof and mixtures thereof can also be additionally used.

Suitable nitrogen-containing complex-forming polycarboxylic acids which can additionally be used are, for example, nitrilotriacetic acid (NTA), ethylenediaminetetraacetic acid, (EDTA), diethylenetriaminepentaacetic acid (DPTA), propylenediaminetetraacetic acid (PDTA), hydroxyethylethylenediaminetriacetic acid (HEDTA), β-alaninediacetic acid, ammonium or alkali metal salts thereof and mixtures thereof.

The wood preservatives of the present invention can additionally contain further auxiliaries such as water, binders, paste-forming agents, organic and inorganic bases, aliphatic carboxylic acids, ammonium or alkali metal salts thereof, plasticizers, fillers, wetting agents, thickeners and mixtures thereof.

The wood preservatives can additionally contain water, which serves to adjust the viscosity and the handling.

Binders and paste-forming agents which can be used are, for example, acrylate resins in the form of aqueous dispersions or powders, plastisols, aminoplastics, phenolic plastics, PVC-containing plasticizers and mixtures thereof.

Organic and inorganic bases which can additionally be used are ammonia, alkali metal hydroxide solution, amines or mixtures thereof. Suitable amines are, for example, mono-, di- and trialkylamines and also alkanolamines.

Suitable alkanolamines are, for example, monoethanolamine, diethanolamine, triethanolamine, isopropanolamine.

To improve the flexibility of the wood preservative dried onto a carrier material, aliphatic $C_5$–$C_{20}$-carboxylic acids such as hexanoic acid, heptanoic acid, octanoic acid, nonanoic acid, decanoic acid, 2-ethylenepentanoic acid, 2-ethylhexanoic acid, 2-ethylheptanoic acid, isooctanoic acid, isononanoic acid, isodecanoic acid, versatic acids (highly branched monocarboxylic acids), dicarboxylic acids ($C_5$–$C_{20}$) e.g. decanedicarboxylic acid, and sebacic acid, can additionally be used. Polycarboxylic acids such as polyacrylic acids or copolymers of acrylic acid with, for example, maleic acid and naphthenoic acids are also suitable.

| Suitable wood preservatives contain, for example |
|---|
| 2–50% by weight, preferably 5–40% by weight, of a copper compound, |
| 2–60% by weight, preferably 5–50% by weight, of a polyamine, |
| 1–65% by weight, preferably 2–55% by weight, of an inorganic fungicide, |

| -continued |
|---|
| Suitable wood preservatives contain, for example |
| 0–25% by weight, preferably 1–20% by weight, of an alkali metal salt of N-cyclohexyldiazenium dioxide, |
| 0–35% by weight, preferably 1–30% by weight, of a complex-forming organic carboxylic acid, its ammonium salts or alkali metal salts, |
| 0–45% by weight, preferably 1–20% by weight, of an auxiliary, |
| 0–50% by weight, preferably 1–40% by weight, of water, |
| the sum of all components yielding 100% by weight. |

If further components are additionally used for the three-part combination copper compound, polyamine and inorganic fungicide, the following wood preservatives have proven suitable:

| Composition consisting of |
|---|
| a) 5–40% by weight of a copper compound<br>5–35% by weight of a polyamine<br>10–50% by weight of an inorganic fungicide<br>5–25% by weight of a complex-forming organic carboxylic acid<br>2.5–35% by weight of water;<br>or |
| b) 5–40% by weight of a copper compound<br>5–35% by weight of a polyamine<br>10–50% by weight of an inorganic fungicide<br>5–25% by weight of a complex-forming organic carboxylic acid<br>2.5–20% by weight of an aliphatic $C_5$–$C_{20}$-carboxylic or dicarboxylic acid<br>2.5–35% by weight of water;<br>or especially when using binders and paste-forming agents |
| c) 5–40% by weight of a copper compound<br>5–35% by weight of a polyamine<br>5–50% by weight of an inorganic fungicide<br>0–5% by weight of an alkali metal salt of n-cyclohexyldiazeniumdioxide<br>0–20% by weight of a complex-forming organic carboxylic acid<br>5–40% by weight of an auxiliary<br>0–30% by weight of water. |

The wood preservatives, which can be present as concentrates or diluted with water as viscous solutions or in the form of pastes, if appropriate also as a solid salt, is best carried out by pre-dissolving a polyamine and, if appropriate, complex-forming organic carboxylic acids or their ammonium or alkali metal salts and, if appropriate, auxiliaries, especially aliphatic $C_5$–$C_{20}$-carboxylic or dicarboxylic acids, using water. The copper compounds are then dissolved therein. The use of water can be dispensed with if the substances employed contain sufficient water (eg. water of crystallization). Solid salts formed from copper compounds, polyamine and, if appropriate, complex-forming organic carboxylic acids or their ammonium or alkali metal salts can also be used.

This premixture can even be present as a highly concentrated paste to which the inorganic fungicides, and if appropriate further auxiliaries, are then added with stirring.

The pH of the wood preservative in the form of the concentrates or pastes is in general between pH 7 and 12. Depending on the application, the concentrates or pastes can on the one hand be applied or introduced directly or with addition of binder on to or into a suitable carrier material. Suitable carrier materials are, for example, plastic films or webs, e.g. of glass fiber, polypropylene, polyester or viscose fiber, foam or other porous plastic materials. In this case, the concentrates are applied to the carrier material, for example, by rolling (calendering). Binders which can be used are, for example, acrylate resins in the form of aqueous dispersions, powders; plastisols, aminoplastics, phenolic plastics, PVC-containing plasticizers.

The system concentrate/carrier material is usually then subjected to drying, for example air drying or, for example, in an oven at about 100–180° C., the concentrate drying on in highly viscous form and being bound to the carrier material; this binding can be improved, if appropriate, by the abovementioned addition of binders, at the same time the release of wood preservative can be delayed after application by this means, if necessary, with a high dose of binder.

The concentrates, in particular on addition of binder, can also be pressed in the form of extrudates, dried and cut to length in order to obtain salt cartridges for insertion into wood by means of boreholes, e.g. in the borehole process. It is also possible to produce cartridges made of powdered mixtures, e.g. when using spray-dried concentrates or using powder ed raw materials in the form of pressed articles of salt.

The diffusible pastes and concentrates or cartridges can be used in the various methods of afterprotection and aftercare when, in the case of particularly endangered wood components, relatively large preservative introduction amounts and penetration depths should be achieved in certain areas.

The pastes are suitable for the bandage process, such as single bandages or multiple bandages, the inoculation injection process, borehole process and the paste process.

Application takes place in the form of preventive or alternatively controlling protective treatments in order
a) permanently to protect timber otherwise not treated with wood preservatives only in specific sections, e.g. roof beam heads;
b) to increase the amounts introduced or penetration depths achieved in the first treatment in the danger areas;
c) in timber which has already been used in construction to supplement or increase the preservative content from the basic protection after a relatively long standing time (period of use);
d) in timber parts which have been used in construction also to reach those areas, in particular in the course of a control measure, which cannot be reached using the customary impregnation process.

The invention is described with the aid of the following examples:

For the tests, the pastes/concentrates were applied in defined amounts to foam as a carrier. The foam with the paste then went through a drying process. The bandage obtained was applied in the soil-air zone after preparation to round wood stocks made of pine which had been used in underground construction. This area was then wound with a self-adhesive PVC film and thus outwardly protected against the penetration of water.

After a standing time of 12 months, the round wood stocks were dug out, repeatedly cut up perpendicular to the grain in the area of the soil-air zone, the wood stock discs were removed and the copper penetration was determined by reacting (spraying) with a 0.2% strength aqueous solution of 4-(2-azopyridyl)resorcinol monosodium salt (copper reagent).

For the tests, pine round wood stocks having a diameter of at least 20 cm and sapwood widths $\geq 3$ cm were used. In each case, an amount of about 500 g of concentrate/salt mixture per bandage was applied, the carrier material was incorporated with the active compound concentrate such that it was about 10 cm above the soil level and about 30 cm below the soil level; the covering film overlapped this area by at least 10 cm in each case. The bandage dimensions here were 40 cm×80 cm. Per formulation, at least 2 bandages were applied to various round wood stocks and tested for penetration power.

EXAMPLE A (not according to the invention)

35% by weight of copper sulfate
32% by weight of potassium bichromate
30% by weight of boric acid
3% by weight of sodium hydrogen sulfate The salt was ground, made into a paste with water, acrylate dispersion (50% strength aqueous dispersion of a copolymer of n-butyl acrylate and styrene) as the binder (10 T concentrate/2 T water/3 T binder), applied to the foam as carrier and dried at 120° C. for at least 15 min. in a continuous flow.

The bandages obtained were applied to round wood stocks. The timber was used for construction after a standing period of 12 months, after cutting up the average copper penetration was determined.

| Copper penetration after a standing time of 12 months | | |
|---|---|---|
| round wood stock 1a: | mean sapwood width: | about 35 mm |
| | mean copper penetration: | about 9 mm |
| | The core was not reached in any position | |
| round wood stock 2a: | mean sapwood width: | about 38 mm |
| | mean copper penetration: | about 12 mm |
| | The core was not reached in any position | |

EXAMPLE B (not according to the invention)

50% by weight of copper suiphate
45% by weight of boric acid
5% by weight of sodium hydrogen sulfate The salt was made into a paste after grinding with water, acrylate dispersion (50% strength aqueous dispersion of a copolymer of n-butyl acrylate and styrene) as the binder (10 T concentrate/ 2 T water/3 T binder), applied to the foam and dried at room temperature for at least 24 h. The bandages were applied.

| Copper penetration after a standing time of 12 months | | |
|---|---|---|
| round wood stock 1b: | mean sapwood width: | about 41 mm |
| | mean copper penetration: | about 7 mm |
| | The core was not reached in any position | |
| round wood stock 2b: | mean sapwood width: | about 37 mm |
| | mean copper penetration: | about 9 mm |
| | The core was not reached in any position | |

EXAMPLE C
(not according to the invention)

50% by weight of copper sulfate
50% by weight of sodium fluoroborate

The salt was made into a paste after grinding with water, acrylate dispersion (50% strength aqueous dispersion of a copolymer of n-butyl acrylate and styrene) as the binder (10 T concentrate(2 T water/3 T binder), applied to the foam and dried at room temperature for at least 24 h. The bandage was applied.

Copper penetration after a standing time of 12 months

| round wood stock 1c: | mean sapwood width: | about 32 mm |
| --- | --- | --- |
| | mean copper penetration: | about 12 mm |
| | The core was not reached in any position | |
| round wood stock 2c: | mean sapwood width: | about 43 mm |
| | mean copper penetration: | about 10 mm |
| | The core was not reached in any position | |

EXAMPLE D
(not according to the invention)

35% by weight of copper acetate
65% by weight of potassium fluoroborate

The salt was made into a paste after grinding with water, acrylate dispersion (50% strength aqueous dispersion of a copolymer of n-butyl acrylate and styrene) as the binder (10 T concentrate(2 T water/3 T binder), applied to the foam and dried at room temperature for at least 24 h. The bandage was applied.

Copper penetration after a standing time of 12 months

| round wood stock 1d: | mean sapwood width: | about 37 mm |
| --- | --- | --- |
| | mean copper penetration: | about 7 mm |
| | The core was not reached in any position | |
| round wood stock 2d: | mean sapwood width: | about 42 mm |
| | mean copper penetration: | about 11 mm |
| | The core was not reached in any position | |

Examples according to the invention

EXAMPLE I

10% by weight of ethanolamine
10% by weight of ethylenediamine
20% by weight of water
10% by weight of copper hydroxycarbonate
50% by weight of boric acid The concentrate was prepared by stirring and applied to foam and dried at room temperature for at least 24 h. The bandage was applied.

Copper penetration after a standing time of 12 months

| round wood stock I 1: | mean sapwood width: | about 33 mm |
| --- | --- | --- |
| | mean copper penetration: virtually identical to the sapwood area The core is reached | |
| round wood stock I 2: | mean sapwood width: | about 35 mm |
| | mean copper penetration: virtually identical to the sapwood area The core is reached | |

EXAMPLE II 25.00% by weight of aminoethylethanolamine
16.65% by weight of water
8.35% by weight of copper hydroxycarbonate
50.00% by weight of boric acid The concentrate was prepared by stirring, applied to foam and dried at room temperature for at least 24 h. The bandage was applied.

Copper penetration after a standing time of 12 months

| round wood stock II 1: | mean sapwood width: | about 41 mm |
| --- | --- | --- |
| | mean copper penetration: virtually identical to the sapwood area The core is reached | |
| round wood stock II 2: | mean sapwood width: | about 31 mm |
| | mean copper penetration: virtually identical to the sapwood area The core is reached | |

EXAMPLE III 32.50% by weight of aminoethylethanolamine
10.00% by weight of lactic acid
17.00% by weight of water
25.00% by weight of boric acid
15.50% by weight of $Cu(OH)_2$, commercially available, stabilized (Manufacturer: Norddeutsche Affinerie)

The concentrate was prepared by stirring and applied to foam and dried at room temperature for at least 24 h. The bandage was applied.

Copper penetration after a standing time of 12 months

| round wood stock III 1: | mean sapwood width: | about 38 mm |
| --- | --- | --- |
| | mean copper penetration: virtually the entire sapwood area was covered and the core boundary was reached. | |
| round wood stock III 2: | mean sapwood width: | about 33 mm |
| | mean copper penetration: virtually the entire sapwood area was covered and the core boundary was reached | |

EXAMPLE IV

| | |
|---|---|
| 7.70% | by weight of dipropylenetriamine |
| 9.80% | by weight of water |
| 2.50% | by weight of isooctanic acid |
| 2.50% | by weight of malic acid |
| 1.00% | by weight of N-cyclohexyldiazeniumdioxy-potassium |
| 5.50% | by weight of copper hydroxide, commercially available, stabilized (Manufacturer: Norddeutsche Affinerie) |
| 38.00% | by weight of sodium fluoride |
| 33.00% | by weight of polyvinyl chloride powder (Vinnolit P 4472 from Vinnolit)/bis-(2-ethylhexyl)phthalate premixture (mixing ratio: about 4:5) |

A paste was prepared by stirring, applied to foam and dried at 130° C. for at least 15 min. in a continuous flow oven. The bandage was applied.

| Copper penetration after a standing time of 12 months | | |
|---|---|---|
| round wood stock IV 1: | mean sapwood width: mean copper penetration: virtually the entire sapwood area was covered and the core boundary was reached. | about 40 mm |
| round wood stock IV 2: | mean sapwood width: mean copper penetration: virtually the entire sapwood area was covered and the core boundary was reached | about 35 mm |

The following examples afford a correspondingly good diffusion power.

EXAMPLE V

| | |
|---|---|
| 14.2% | by weight of dipropylenetriamine |
| 8.9% | by weight of malic acid |
| 18.9% | by weight of copper hydroxide carbonate $[Cu(OH)_2CuCO_3]$ |
| 100% | by weight of water |
| 35.0% | by weight of sodium fluoride |
| 13.0% | by weight of boric acid |

Deviating from the previously mentioned applications, this time 500 g of the similarly prepared paste were applied directly to the round wood stock and covered with a plastic film. The incorporation conditions were identical to those described previously.

| Copper penetration after a standing time of 12 months | |
|---|---|
| Round wood stock V 1: | mean sapwood width: about 39 mm mean copper penetration: virtually the entire sapwood area was covered and the core boundary was reached. |
| Round wood stock V 2: | mean sapwood width: about 37 mm mean copper penetration: virtually the entire sapwood area was covered and the core boundary was reached. |

EXAMPLE VI

| | |
|---|---|
| 22.50% | by weight of 1,3-diaminopropane |
| 24.00% | by weight of water |
| 10.00% | by weight of malic acid |
| 3.50% | by weight of N-cyclohexyldiazeniumdioxy-potassium |
| 15.00% | by weight of copper hydroxide, commercially available, stabilized (Manufacturer: Norddeusche Affinerie) |
| 25.00% | by weight of boric acid |

A paste was prepared by stirring, applied to foam and dried in a continuous flow oven at 140° C.

EXAMPLE VII

| | |
|---|---|
| 22.50% | by weight of 1,3-diaminopropane |
| 21.00% | by weight of water |
| 7.50% | by weight of nitrilotriacetic acid |
| 4.00% | by weight of N-cyclohexyldiazenium-dioxy-potassium |
| 5.00% | by weight of glycerol |
| 25.00% | by weight of boric acid |
| 15.00% | by weight of copper hydroxide, commercially available, stabilized (Manufacturer: Norddeutsche Affinerie) |

A paste was prepared by stirring, applied to foam and dried for at least 15 min in a continuous flow oven at 130° C.

EXAMPLE VIII

| | |
|---|---|
| 17.00% | by weight of 1,3-diaminopropane |
| 7.00% | by weight of monoethanolamine |
| 26.00% | by weight of water |
| 8.50% | by weight of malic acid |
| 2.50% | by weight of bis(N-cyclohexyldiazenium-dioxy)copper |
| 25.00% | by weight of boric acid |
| 14.00% | by weight of copper hydroxide, commercially available, stabilized (Manufacturer: Norddeutsche Affinerie) |

A paste was prepared by stirring, applied to foam and dried for at least 10 minutes in a continuous flow oven at 130° C.

EXAMPLE IX

| | |
|---|---|
| 16.70% | by weight of dipropylenetriamine |
| 11.80% | by weight of water |
| 8.00% | by weight of isooctanoic acid |
| 5.00% | by weight of malic acid |
| 16.60% | by weight of boric acid |
| 8.60% | by weight of copper hydroxide, commercially available, stabilized Manufacturer: Norddeutsche Affinerie) |
| 33.30% | by weight of polyvinyl chloride powder (Vinnolit P 4472 from Vinnolit)/bis(2-ethylhexyl) phthalate premixture (mixing ratio: about 4:5) |

A paste was prepared by stirring, applied to foam and dried for at least 15 min at 130° C. in a continuous flow oven.

EXAMPLE X

| |
|---|
| 18.5% by weight of dipropylenetriamine |
| 5.3% by weight of water |
| 7.7% by weight of isooctanoic acid |
| 7.5% by weight of malic acid |
| 11.5% by weight of copper hydroxide, stabilized |
| 36.5% by weight of sodium fluoride |
| 13.0% by weight of boric acid |

A paste was prepared by stirring, applied to foam and dried for at least 15 min in a continuous flow oven at 130° C.

EXAMPLE XI

| |
|---|
| 15.4% by weight of dipropylenetriamine |
| 23.9% by weight of water |
| 35.7% by weight of copper citrate (about 35% Cu) (copper (II) citrate 2,5-hydrate) |
| 25.0% by weight of boric acid |

A paste was prepared by stirring, applied to foam and dried for at least 15 min in a continuous flow oven at 130° C.

EXAMPLE XII

| |
|---|
| 16.5% by weight of diethylenetriamine |
| 27.5% by weight of water |
| 15.0% by weight of malic acid |
| 16.0% by weight of copper hydroxide, stabilized |
| 25.0% by weight of boric acid |

A paste was prepared by stirring, applied to foam and dried for at least 15 min in a continuous flow oven at 130° C.

EXAMPLE XIII

| |
|---|
| 21.0% by weight of dipropylenetriamine |
| 28.0% by weight of water |
| 13.2% by weight of citric acid monohydrate |
| 16.8% by weight of copper hydroxide (stabilized) |
| 21.0% by weight of Polybor ($Na_2B_9O_{13} \times 4\ H_2O$) |

A paste was prepared by stirring, applied to foam and dried for at least 15 min in a continuous flow oven at 130° C.

EXAMPLE XIV

| |
|---|
| 19.0% by weight of dipropylenetriamine |
| 11.9% by weight of malic acid |
| 16.9% by weight of copper hydroxide carbonate |
| 32.2% by weight of water |
| 20.0% by weight of sodium fluoride |

A paste was prepared by stirring, applied to foam and dried for at least 15 min in a continuous flow oven at 130° C.

We claim:

1. A process for the afterprotection of wood, which comprises treating the wood with an effective wood preserving amount of a wood preservative composition comprising a copper compound, a polyamine or alkanolamine having at least two nitrogen atoms, and an inorganic fungicide, the treatment being effected by means of a bandaging process, an inoculation injection process, a borehole process or a paste process.

2. The process defined in claim 1, wherein the wood preservative composition further comprises a complex forming organic carboxylic acid.

3. The process defined in claim 1, wherein the copper compound is selected from the group consisting of copper sulfate, copper acetate, copper citrate, copper naphthenate, copper hydroxide, copper hydroxycarbonate, copper oxychloride, copper oxide, copper borate, copper fluoride, copper fluoroborate, bis(N-cyclohexyldiazeniumdioxy) copper and mixtures thereof.

4. The process defined in claim 1, wherein the polyamine or alkanolamine is selected from the group consisting of $C_2$–$C_9$ alkylenepolyamine, alkanolamine and mixtures thereof.

5. The process defined in claim 1, wherein the polyamine or alkanolamine is selected from the group consisting of ethylenediamine, 2-diethylaminoethylamine, diethylenetriamine, triethylenetetramine, tetraethylpentamine, 1,2-diaminopropane, 1,3-diaminopropane, dipropylenetriamine, tripropylenetetramine, 3-(2-aminoethyl)aminopropylamine, N,N'-bis(3-aminopropyl)-1,3-propanediamine, aminoethylethanolamine and mixtures thereof.

6. The process defined in claim 5, wherein the polyamine or alkanolamine is selected from the group consisting of ethylenediamine, diethylenetriamine, 1,3-diaminopropane, dipropylenetriamine, aminoethylethanolamine and mixtures thereof.

7. The process defined in claim 1, wherein the inorganic fungicide is selected from the group consisting of boron compounds, fluorides, fluoroborates, fluorophosphates, difluorophosphates and mixtures thereof.

8. The process defined in claim 2, wherein the complex-forming organic carboxylic acid is selected from the group consisting of hydroxycarboxylic acids, aminocarboxylic acids, nitrogen-containing polycarboxylic acids, ammonium and alkali metal salts thereof and mixtures thereof.

9. The process defined in claim 8, wherein the complex-forming organic carboxylic acid is selected from the group consisting of glyoxylic acid, lactic acid, malic acid, tartaric acid, citric acid, nitriloacetic acid, ethylenediaminetetraacetic acid, diethylenetriaminepentaacetic acid, propylenediaminetetraacetic acid, hydroxyethylethylenediaminetriacetic acid, β-alaninediacetic acid, sarcosine, glycine ammonium and alkali metal salts thereof and mixtures thereof.

10. The process defined in claim 1, wherein the wood preservative composition further comprises auxiliaries selected from the group consisting of water, binders, paste-forming agents, organic and inorganic bases, aliphatic carboxylic acids, plasticizers, fillers, wetting agents, thickeners and mixtures thereof.

11. The process defined in claim 1, wherein the wood preservative composition consists of
  from 2 to 50% by weight of one or more copper compounds,
  from 2 to 60% by weight of one or more polyamines or alkanolamines, from 1 to 65% by weight of one or more inorganic fungicides, from 0 to 25% by weight of one or more alkali metal salts of N-cyclohexyldiazenium dioxide, from 0 to 35% by weight of one or more complex-forming organic carboxylic acids or ammonium or alkali metal salts thereof, from 0 to 25% by weight of one or more auxiliaries, and from 0 to 50% by weight of water.

12. The process defined claim 1 wherein the treatment is effected by means of the bandaging process.

13. A bandage for the afterprotection of wood, comprising an effective wood preserving amount of a wood preservative composition comprising a copper compound, a polyamine or alkanolamine having at least two nitrogen atoms, and an inorganic fungicide.

14. The bandage defined in claim 13, wherein the wood preservative composition further comprises a complex forming organic carboxylic acid.

15. The bandage defined in claim 13, wherein the copper compound is selected from the group consisting of copper sulfate, copper acetate, copper citrate, copper naphthenate, copper hydroxide, copper hydroxycarbonate, copper oxychloride, copper oxide, copper borate, copper fluoride, copper fluoroborate, bis(N-cyclohexyldiazeniumdioxy) copper and mixtures thereof.

16. The bandage defined in claim 13, wherein the polyamine or alkanolamine is selected from the group consisting of $C_2$–$C_9$ alkylenepolyamine, alkanolamine and mixtures thereof.

17. The bandage defined in claim 13, wherein the polyamine or alkanolamine is selected from the group consisting of ethylenediamine, 2-diethylaminoethylamine, diethylenetriamine, triethylenetetramine, tetraethylpentamine, 1,2-diaminopropane, 1,3-diaminopropane, dipropylenetriamine, tripropylenetetramine, 3-(2-aminoethyl)aminopropylamine, N,N'-bis(3-aminopropyl)-1,3-propanediamine, aminoethylethanolamine and mixtures thereof.

18. The bandage defined in claim 17, wherein the polyamine or alkanolamine is selected from the group consisting of ethylenediamine, diethylenetriamine, 1,3-diaminopropane, dipropylenetriamine, aminoethylethanolamine and mixtures thereof.

19. The bandage defined in claim 13, wherein the inorganic fungicide is selected from the group consisting of boron compounds, fluorides, fluoroborates, fluorophosphates, difluorophosphates and mixtures thereof.

20. The bandage defined in claim 14, wherein the complex-forming organic carboxylic acid is selected from the group consisting of hydroxycarboxylic acids, aminocarboxylic acids, nitrogen-containing polycarboxylic acids, ammonium and alkali metal salts thereof and mixtures thereof.

21. The bandage defined in claim 20, wherein the complex-forming organic carboxylic acid is selected from the group consisting of glyoxylic acid, lactic acid, malic acid, tartaric acid, citric acid, nitriloacetic acid, ethylenediaminetetraacetic acid, diethylenetriaminepentaacetic acid, propylenediaminetetraacetic acid, hydroxyethylethylenediaminetriacetic acid, β-alaninediacetic acid, sarcosine, glycine ammonium and alkali metal salts thereof and mixtures thereof.

22. The bandage defined in claim 13, wherein the wood preservative composition further comprises auxiliaries selected from the group consisting of water, binders, paste-forming agents, organic and inorganic bases, aliphatic carboxylic acids, plasticizers, fillers, wetting agents, thickeners and mixtures thereof.

23. The bandage defined in claim 13, wherein the wood preservative composition consists of from 2 to 50% by weight of one or more copper compounds, from 2 to 60% by weight of one or more polyamines or alkanolamines, from 1 to 65% by weight of one or more inorganic fungicide, from 0 to 25% by weight of one or more alkali metal salt of N-cyclohexyldiazenium dioxide, from 0 to 35% by weight of one or more complex-forming organic carboxylic acids or ammonium or alkali metal salts thereof, from 0 to 25% by weight of one or more auxiliaries, and from 0 to 50% by weight of water.

* * * * *

UNITED STATES PATENT AND TRADEMARK OFFICE
CERTIFICATE OF CORRECTION

PATENT NO.    : 6,110,263
DATED         : August 29, 2000
INVENTOR(S)   : Goettsche et al.

It is certified that error appears in the above-identified patent and that said Letters Patent is hereby corrected as shown below:

<u>Column 14, claim 23,</u>
Line 31, after "one or more" insert -- of the --.

Signed and Sealed this

Eighteenth Day of September, 2001

Attest:

*Nicholas P. Godici*

NICHOLAS P. GODICI
*Attesting Officer*    *Acting Director of the United States Patent and Trademark Office*